US009226707B2

(12) United States Patent
Huang

(10) Patent No.: US 9,226,707 B2
(45) Date of Patent: *Jan. 5, 2016

(54) DEVICE AND SYSTEM TO REDUCE TRAUMATIC BRAIN INJURY

(71) Applicant: Chiming Huang, Shawnee Mission, KS (US)

(72) Inventor: Chiming Huang, Shawnee Mission, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/554,141

(22) Filed: Nov. 26, 2014

(65) Prior Publication Data

US 2015/0080768 A1  Mar. 19, 2015

Related U.S. Application Data

(63) Continuation-in-part of application No. 14/198,045, filed on Mar. 5, 2014.

(60) Provisional application No. 61/816,544, filed on Apr. 26, 2013.

(51) Int. Cl.
| A61B 5/00 | (2006.01) |
| A61B 5/103 | (2006.01) |
| A61B 5/117 | (2006.01) |
| A61F 5/00 | (2006.01) |
| A61B 5/11 | (2006.01) |
| A42B 3/04 | (2006.01) |
| A61B 6/00 | (2006.01) |

(52) U.S. Cl.
CPC ............... *A61B 5/4836* (2013.01); *A42B 3/046* (2013.01); *A42B 3/0473* (2013.01); *A61B 5/0024* (2013.01); *A61B 5/103* (2013.01); *A61B 5/11* (2013.01); *A61B 5/4064* (2013.01); *A61B 5/6803* (2013.01); *A61B 5/7282* (2013.01); *A61B 5/002* (2013.01); *A61B 5/1116* (2013.01); *A61B 6/5217* (2013.01); *A61B 2562/0219* (2013.01)

(58) Field of Classification Search
CPC ........................................................ A61B 5/00
USPC ......... 600/300, 301, 587, 595; 602/17, 18, 19
See application file for complete search history.

(56) References Cited

U.S. PATENT DOCUMENTS

| 2,820,455 | A | * | 1/1958 | Hall ................................. 602/18 |
| 3,645,259 | A | * | 2/1972 | Schulman .................... 128/869 |
| 3,873,996 | A | * | 4/1975 | Varteressian ..................... 2/421 |
| 3,900,896 | A | * | 8/1975 | Ackerman ......................... 2/468 |
| 3,957,040 | A | * | 5/1976 | Calabrese ........................ 602/36 |
| 4,219,193 | A | * | 8/1980 | Newman ......................... 482/10 |
| 4,383,523 | A | * | 5/1983 | Schurman ........................ 602/36 |

(Continued)

Primary Examiner — Rene Towa
Assistant Examiner — May Abouelela
(74) Attorney, Agent, or Firm — Hovey Williams LLP

(57) ABSTRACT

A device for reducing traumatic brain injury comprises a first sensor, a first linkage element, and a processing element. The first sensor is coupled to a head component and configured to measure an acceleration of a user's head as a result of an impact on the head component and to generate corresponding first sensor measurements. The first linkage element is configured to connect the head component to a body component and is able to switch between a first state in which it is relatively flexible and a second state in which it is relatively rigid. The first linkage element is switched from its first state to its second state by a locking signal. The processing element is configured to receive the first sensor measurements and to generate the locking signal when a value of the first sensor measurements is greater than or equal to an injury level.

19 Claims, 8 Drawing Sheets

(56) References Cited

U.S. PATENT DOCUMENTS

| | | | | |
|---|---|---|---|---|
| 5,123,408 A * | 6/1992 | Gaines | | 602/17 |
| 5,158,089 A * | 10/1992 | Swezey et al. | | 600/595 |
| 5,242,377 A * | 9/1993 | Boughner et al. | | 602/17 |
| 5,248,293 A * | 9/1993 | Hubbard et al. | | 602/17 |
| 5,261,125 A * | 11/1993 | Cartwright et al. | | 2/421 |
| 5,272,770 A * | 12/1993 | Allen et al. | | 2/421 |
| 5,371,905 A * | 12/1994 | Keim | | 2/413 |
| 5,425,378 A * | 6/1995 | Swezey et al. | | 600/595 |
| 5,832,926 A * | 11/1998 | Towlen | | 128/845 |
| 5,919,144 A * | 7/1999 | Bridger et al. | | 600/561 |
| 6,006,368 A * | 12/1999 | Phillips | | 2/468 |
| 6,052,835 A * | 4/2000 | O'Shea | | 2/468 |
| 6,730,047 B2 * | 5/2004 | Socci et al. | | 600/595 |
| 6,786,877 B2 * | 9/2004 | Foxlin | | 600/587 |
| 6,968,576 B2 * | 11/2005 | McNeil et al. | | 2/425 |
| 6,971,123 B2 * | 12/2005 | Weaver | | 2/468 |
| 7,155,747 B2 * | 1/2007 | Baker | | 2/422 |
| 7,371,221 B1 * | 5/2008 | Baker | | 602/18 |
| 7,380,290 B2 * | 6/2008 | Mothaffar | | 2/421 |
| 7,383,728 B2 * | 6/2008 | Noble et al. | | 73/379.01 |
| 7,395,558 B2 * | 7/2008 | Mothaffar | | 2/421 |
| 7,430,767 B2 * | 10/2008 | Nagely | | 2/425 |
| 7,449,005 B2 * | 11/2008 | Pickering et al. | | 602/18 |
| 7,488,294 B2 * | 2/2009 | Torch | | 600/558 |
| 7,849,525 B2 * | 12/2010 | Ghajar | | 2/416 |
| 7,941,873 B2 * | 5/2011 | Nagely et al. | | 2/425 |
| 8,057,415 B2 * | 11/2011 | Hipp et al. | | 602/18 |
| 8,074,301 B2 * | 12/2011 | Mothaffar | | 2/468 |
| 8,191,180 B2 * | 6/2012 | Berry | | 2/468 |
| 8,316,691 B2 * | 11/2012 | Jeftic-Stojanovski et al. | | 73/12.04 |
| 8,537,017 B2 * | 9/2013 | Mack et al. | | 340/573.1 |
| 8,548,768 B2 * | 10/2013 | Greenwald et al. | | 702/141 |
| 8,556,831 B1 * | 10/2013 | Faber et al. | | 600/587 |
| 2002/0183657 A1 * | 12/2002 | Socci et al. | | 600/595 |
| 2003/0088906 A1 * | 5/2003 | Baker | | 2/416 |
| 2004/0225236 A1 * | 11/2004 | Wheeler et al. | | 600/595 |
| 2005/0177929 A1 * | 8/2005 | Greenwald et al. | | 2/425 |
| 2006/0074338 A1 * | 4/2006 | Greenwald et al. | | 600/549 |
| 2006/0189852 A1 * | 8/2006 | Greenwald et al. | | 600/300 |
| 2007/0015611 A1 * | 1/2007 | Noble et al. | | 473/450 |
| 2008/0208013 A1 * | 8/2008 | Zhang et al. | | 600/301 |
| 2009/0158509 A1 * | 6/2009 | Ghajar | | 2/422 |
| 2010/0198104 A1 * | 8/2010 | Schubert et al. | | 600/558 |
| 2010/0204628 A1 * | 8/2010 | Ghajar | | 602/18 |
| 2010/0263110 A1 * | 10/2010 | Berry | | 2/459 |
| 2010/0286581 A1 * | 11/2010 | Hipp et al. | | 602/18 |
| 2010/0312145 A1 * | 12/2010 | Ernst et al. | | 600/587 |
| 2011/0184319 A1 * | 7/2011 | Mack et al. | | 600/595 |
| 2011/0184320 A1 * | 7/2011 | Shipps et al. | | 600/595 |
| 2011/0219852 A1 * | 9/2011 | Kasten | | 73/12.04 |
| 2011/0288459 A1 * | 11/2011 | Jenkins, III | | 602/18 |
| 2012/0174302 A1 * | 7/2012 | Jenkins, III | | 2/468 |
| 2012/0191397 A1 * | 7/2012 | Eatwell | | 702/94 |
| 2012/0245439 A1 * | 9/2012 | Andre et al. | | 600/310 |
| 2013/0060168 A1 * | 3/2013 | Chu et al. | | 600/595 |
| 2013/0150684 A1 * | 6/2013 | Cooner | | 600/301 |
| 2013/0303946 A1 * | 11/2013 | Gettens et al. | | 600/587 |
| 2014/0039355 A1 * | 2/2014 | Crisco et al. | | 600/595 |
| 2014/0081180 A1 * | 3/2014 | Ghajar | | 600/595 |

* cited by examiner

DEVICE AND SYSTEM TO REDUCE TRAUMATIC BRAIN INJURY

RELATED APPLICATION

The current patent application is a continuation-in-part and claims priority benefit, with regard to all common subject matter, of U.S. patent application Ser. No. 14/198,045, titled "DEVICE AND SYSTEM TO REDUCE TRAUMATIC BRAIN INJURY", filed Mar. 5, 2014. The earlier-filed patent application is hereby incorporated by reference, in its entirety, into the current patent application.

BACKGROUND OF THE INVENTION

1. Field of the Invention

Embodiments of the current invention relate to devices and systems configured to reduce traumatic brain injury.

2. Description of the Related Art

Closed-head traumatic brain injury (TBI) is typically a result of the brain impacting the interior of the skull. Forces acting on the body or the head generally accelerate the brain. High positive acceleration or negative acceleration may cause the brain to contact the skull with enough force to cause damage. The types of damage may be categorized as concussive TBI, blast TBI, or mild TBI. Concussive TBI may be suffered by athletes in sports such as hockey, boxing, or American football. Blast TBI may be experienced by military or law enforcement personnel while on patrol or traveling in a vehicle. Mild TBI may be experienced by anyone suffering a fall, a minor vehicular accident, or the like. Furthermore, the direction and location of the impact and the resulting motion of the head may determine the severity of the injury. Studies have shown that a side impact to the head, or the body, that results in the head rotating (about the roll axis) to the left or right shoulder may lead to a greater chance of suffering a TBI, as compared with impacts from other directions.

Helmets are available to athletes, military personnel, law enforcement personnel, and the like. While helmets generally provide protection for skull fractures upon direct impact, they do not provide protection from rotational forces to the head and may not reduce the occurrence or severity of a concussive TBI (cTBI). Even when wearing a helmet, the head, and the brain within, may experience an acceleration of a great enough magnitude to cause a cTBI.

Implementing a rigid linkage between the helmet and the body of the helmeted person has been proposed in prior art as a means to reduce concussive traumatic injuries [e.g., U.S. Pat. No. 7,941,873 to Nagely et al. or U.S. Patent Application Publication No. 2010/0204628 to Ghajar]. In concussions, however, impact energy can act on the head within 20-50 milliseconds of impact [Rowson S, Brolinson G, Goforth M, Dietter D, Duma S (2009) Linear and angular head acceleration measurements in collegiate football, J Biomech Eng 131: 061016, doi: 10.1115/1.3130454].

SUMMARY OF THE INVENTION

Embodiments of the current invention solve the above-mentioned problems and provide methods, devices, and systems that are utilized with head gear and body wear to reduce traumatic brain injury. Methods that offer improvement over the prior art involve the use of one or more impedance-matched linkage elements for dissipating impact energy before such energy can injure the brain. Methods may further include, but are not limited to, the use of electrical, electromagnetic, magnetorheological or other non-Newtonian fluids, fast-acting hydraulic mechanisms or other means which do not involve moving macroscopic parts which can require a response time longer than 20-50 milliseconds.

A first embodiment of the current invention provides a device for reducing traumatic brain injury and broadly comprises a first sensor, a first linkage element, and a processing element. The first sensor is coupled to a head component and configured to measure an acceleration of a user's head as a result of an impact on the head component and to generate corresponding first sensor measurements. The first linkage element is configured to connect the head component to a body component and is able to switch between a first state in which it is relatively flexible and a second state in which it is relatively rigid. The first linkage element is switched from its first state to its second state by a locking signal. The processing element is configured to receive the first sensor measurements and to generate the locking signal when a value of the first sensor measurements is greater than or equal to an injury level.

A second embodiment of the current invention provides a system for reducing traumatic brain injury and comprises a head component, a body component, a first sensor, a first linkage element, and a processing element. The head component is worn on a user's head, and the body component is worn on the user's body. The first sensor is coupled to a head component and configured to measure an acceleration of a user's head as a result of an impact on the head component and to generate corresponding first sensor measurements. The first linkage element is configured to connect the head component to a body component and is able to switch between a first state in which it is relatively flexible and a second state in which it is relatively rigid. The first linkage element is switched from its first state to its second state by a locking signal. The processing element is configured to receive the first sensor measurements and to generate the locking signal when a value of the first sensor measurements is greater than or equal to an injury level.

A third embodiment of the current invention provides a method of reducing traumatic brain injury comprising the steps of generating sensor measurements from a first sensor in response to an impact to a head component attached to the head of a user, determining if a value of the sensor measurements is greater than or equal to an injury level, transmitting a locking signal to a linkage element when the value of the sensor measurements is greater than or equal to the injury level, and switching a state of the linkage element connecting the head component to a body component attached to the body of the user when the locking signal is received from a relatively flexible state to a relatively rigid state.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

Figure 1:
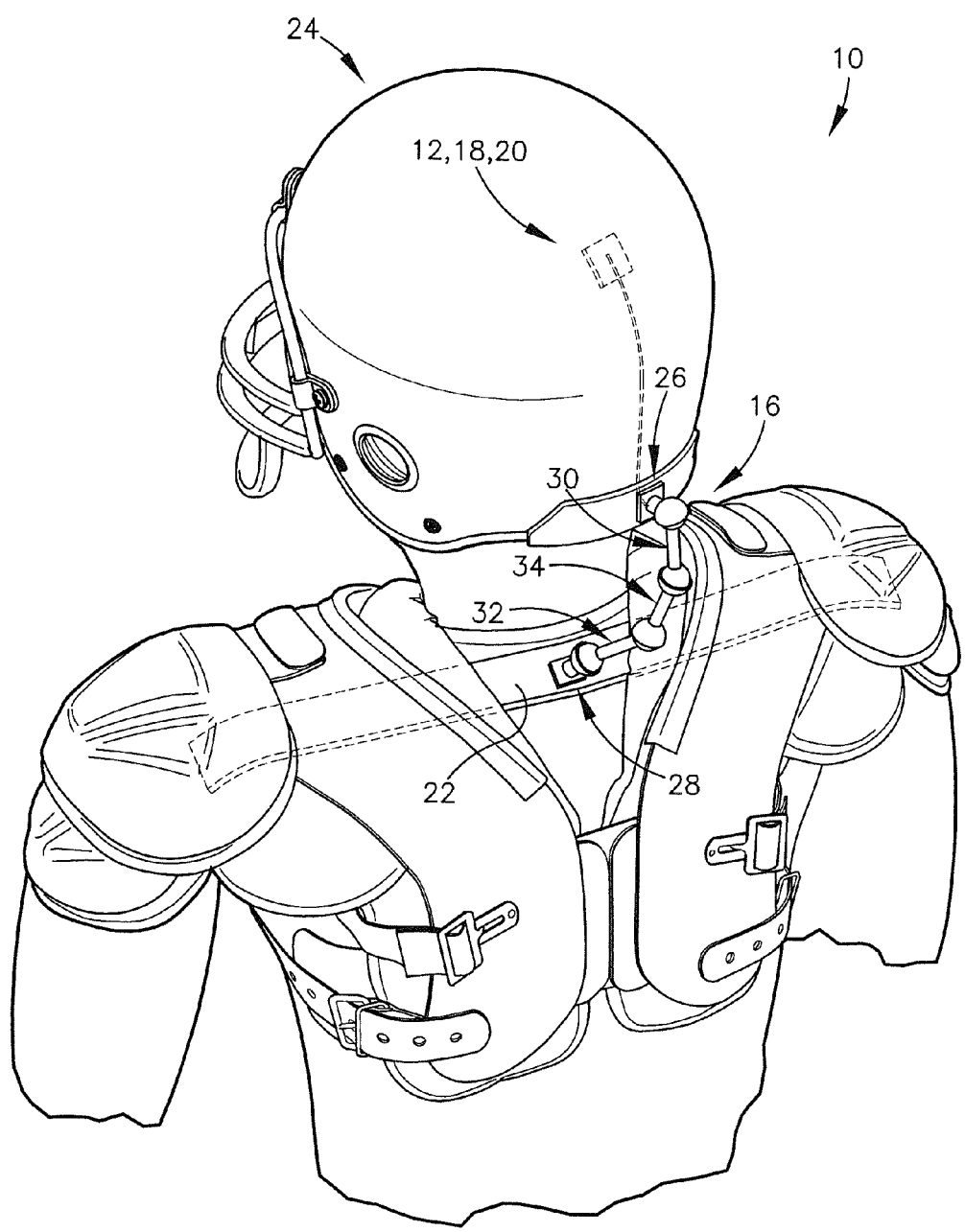
FIG. 1 is a perspective view of a device for reducing traumatic brain injury constructed in accordance with a first embodiment of the current invention and utilized with an American football helmet and shoulder pads, the device including a first sensor and one linkage mechanism.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Figure 2:
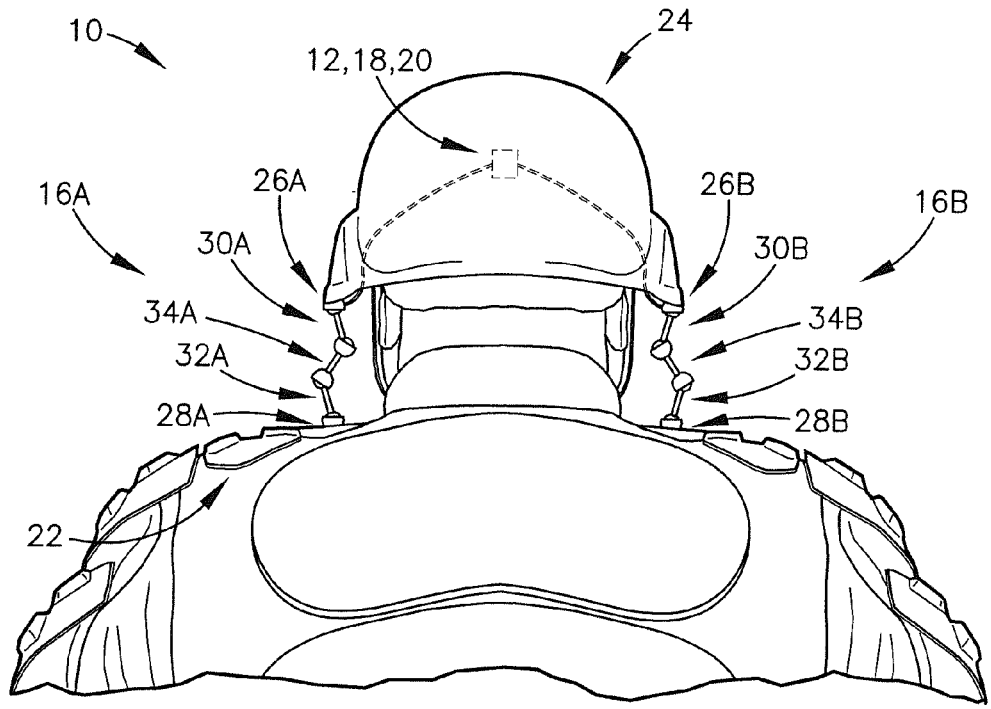
FIG. 2 is a rear view of a first alternative embodiment of the device of FIG. 1 utilized with military or law enforcement body armor, the device including two linkage mechanisms.
Figure 3:
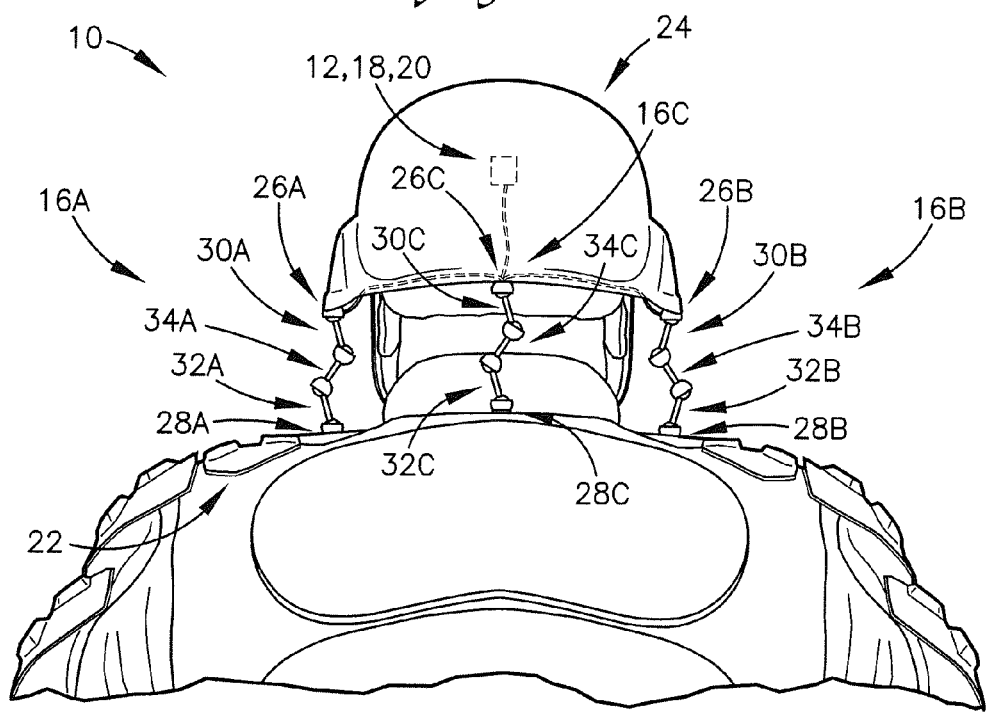
FIG. 3 is a rear view of a second alternative embodiment of the device of FIG. 1 utilized with military or law enforcement body armor, the device including three linkage mechanisms.

A device 10 for reducing traumatic brain injury constructed in accordance with a first embodiment of the current invention is shown in FIGS. 1-3 and broadly comprises a first sensor 12, a second sensor 14, one or more linkage elements 16, a processing element 18, and a memory element 20. The device 10 may be utilized by a user engaging in activity during which an impact to the head is possible. The activity may include contact sports such as hockey, boxing, American football, snow or ice-related sports such as skiing, snowboarding, sledding, sports in which falling or landing on the head is possible such as skateboarding, bicycling, equestrian activities, motorcycle riding, automobile driving, military combat, and the like. When the device 10 is utilized playing a sport in which there might not be equipment on the body to which the device 10 can couple, such as the shoulder pads in American football, the device 10 may further comprise a body component 22. The device 10 may also couple to protective equipment that the user may already wear for the activity including a head component 24, such as a helmet or other headgear.

The first sensor 12, as seen in FIGS. 1-3 and 6, generally measures a linear as well as a rotational acceleration of the user's head due to an impact. In some embodiments, the first sensor 12 may also, or alternatively, measure a velocity of the user's head or a force of the impact. The first sensor 12 may include motion sensors, velocity sensors, vibration sensors, shock sensors, accelerometers, gyroscope chips, magnetometer chips, inclinometers, angle rate sensors, angular velocity sensors, or the like, or combinations thereof. The first sensor 12 may include technology such as strain gauges, piezoelectric elements, micro electro-mechanical systems (MEMS), nanotechnologies in which a material, solid or liquid, can change it stiffness while modulated by electromagnetic fields, or the like, or combinations thereof. The first sensor 12 may measure linear acceleration, velocity, or force along a single axis or multiple axes, such as any three mutually orthogonal axes, e.g., the X, Y, Z axes, and may record, communicate, or output a sensor measurement. Each sensor measurement may include a plurality of values which may be in the form of vector data or magnitude data. Thus, in various embodiments, the first sensor 12 may generate three or more values for the three linear measurements. In addition or instead, the first sensor 12 may measure angular or rotational acceleration along mutually orthogonal axes, such as pitch, roll, and yaw. With regard to measuring the acceleration of the head, pitch is nodding to gesture yes, roll is bending the head-and-neck toward one or the other shoulder, and yaw is gesturing no or turning the head to watch cars from both directions before crossing a street. Accordingly, the first sensor 12 may generate three or more values for the three angular measurements.

The sensor measurements be an analog value, a digital value, a pulse-width modulation (PWM) value, or the like. The first sensor 12 may output the sensor measurements at a frequency ranging from 500 hertz (Hz) to 20 kilohertz (kHz) or higher. This range of frequencies should be great enough to detect an impulse-like impact, whose duration may be range from a fraction of a millisecond to single digits of milliseconds. The first sensor 12 may also include electronic circuitry such as amplifiers, analog-to-digital converters (ADCs), or other conversion circuits.

The first sensor 12 may be positioned within the interior of the head component 24 of the user. The head component 24 may be headwear, headgear, a helmet, such as a sports helmet, a motorcycle or automobile helmet, or a combat helmet, or the like. In some embodiments, the first sensor 12 may further include first and second resilient members, such as springs, that are coupled to opposing sides of the first sensor 12. The first resilient member may contact an inner surface of the head component 24, and the second resilient member may contact the user's head. In other embodiments, the first sensor 12, with or without resilient members, may be coupled to padding on the interior of the head component 24, or coupled to a hard shell of the head component 24, such that when the head component 24 is worn, the first sensor 12 may contact the user's head in order to detect force and other physical parameters related to the force applied to the head or the helmet (it may be advantageous for the first sensor 12 to also analyze the force at the helmet, which is typically of a greater magnitude than the force at the head).

Figure 4:
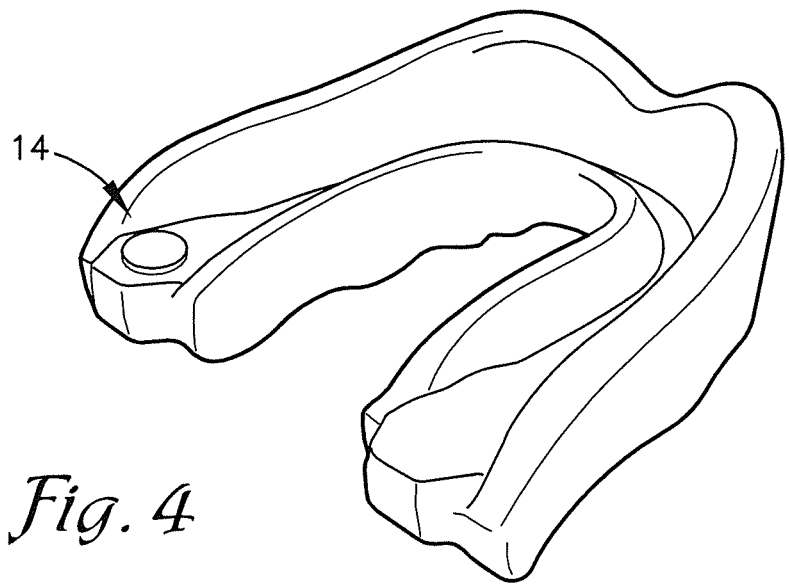
FIG. 4 is a perspective view of a second sensor of the device of FIG. 1 being utilized with a mouthpiece to be worn in a user's mouth.
Figure 6:
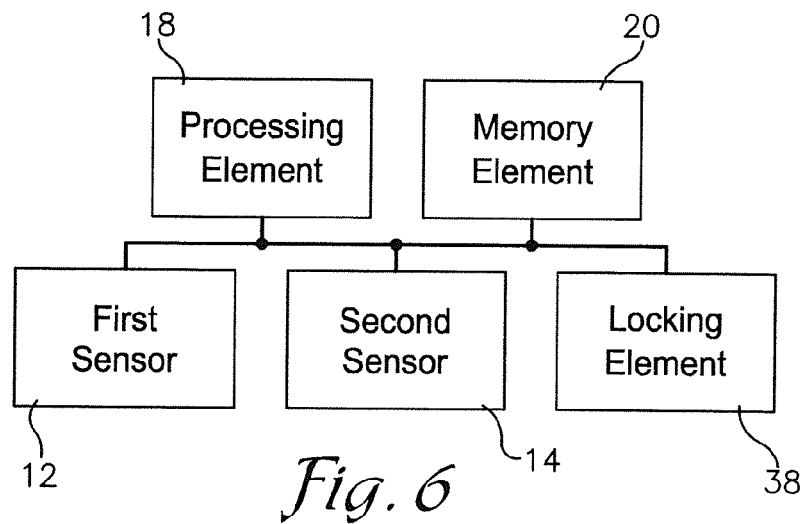
FIG. 6 is a schematic block diagram of other components of the device of FIG. 1.
Figure 8:
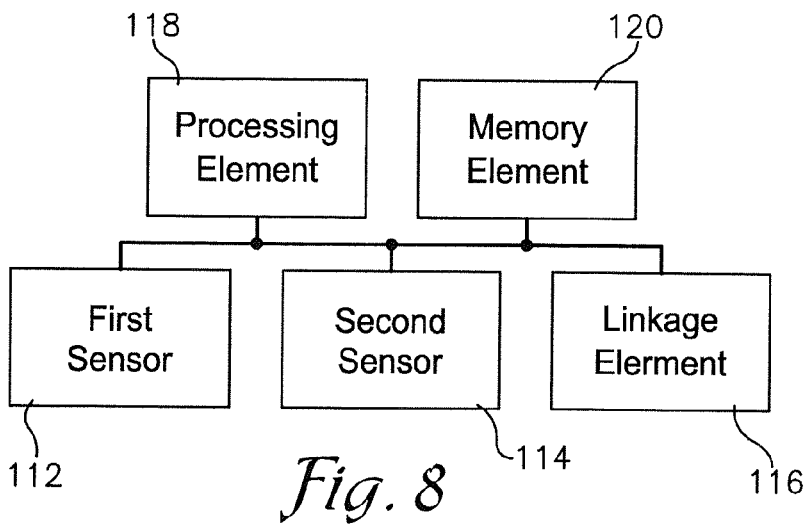
FIG. 8 is a schematic block diagram of other components of the device of FIG. 7.

The second sensor 14, as seen in FIGS. 4 and 6, may be substantially similar to the first sensor 12 in structure and function and may be positioned within the mouth of the user. In some embodiments, the second sensor 14 may be considered optional. The second sensor 14 may include, be coupled with, or be integrated in a mouthpiece or mouthguard, which is worn in the mouth or on the teeth of the user. Furthermore, the second sensor 14 may include or be in communication with a wireless transmitter to transmit sensor measurements to the processing element 18. The wireless transmitter may transmit radio frequency (RF) signals and/or data utilizing known communication standards.

The linkage element 16, as seen in FIGS. 1-3 and 5, generally provides a link between the user's head and the user's body that is normally flexible but becomes rigid upon an impact to the head. If just one linkage element 16 is utilized, as in FIG. 1, then it is generally positioned at the rear of the user's head and the upper central portion of the user's back. If more than one linkage element 16 is utilized, such as in FIGS. 2 and 3, then the device 10 may include a left linkage element 16A positioned on the left side of the user's head and the user's left shoulder, a right linkage element 16B positioned on the right side of the user's head and the user's right shoulder, and a center linkage element 16C positioned at the rear of the user's head and the upper central portion of the user's back. In some embodiments, only the left linkage element 16A and the right linkage element 16B are utilized, as shown in FIG. 2. Generally, each linkage element 16 may be formed from material or components whose stiffness or rigidity can be controlled, that is, increased and decreased. In exemplary embodiments, each linkage element 16 may be formed from a plurality of components and may include a first anchor 26, a second anchor 28, a first end link 30, a second end link 32, and at least one middle link 34. In other embodiments, the linkage element 16 may be formed from a single component with material that has a variable stiffness or rigidity.

While the linkage element 16 is in a flexible state, it may seem limp or relaxed and may assume a variety of shapes, positions, and orientations as the user moves his head with respect to his body. This allows the user to have a wide range of motion and freedom of head movement while wearing the device 10. When the linkage element 16 is in a rigid state, it may maintain the same shape it was in when it transformed from the flexible state to the rigid state. However, the linkage element 16 is in the rigid state for only a short period of time, as discussed in greater detail below.

The first anchor 26, as seen in FIGS. 1-3 and 5, generally retains the first end link 30. The first anchor 26 may include an anchor socket 36 and a locking element 38. The anchor socket 36 may include a concave, partially spherical chamber which is configured to retain at least a portion of the first end link 30. The anchor socket 36 may allow rotational, pivotal, and conical motion of the first end link 30. The locking element 38 generally locks the first end link 30 in position within the anchor socket 36, restricting or stopping motion of the first end link 30 therein. The locking element 38 may include an electromagnet 40 which can selectively lock the first end link 30 in position within the anchor socket 36. The electromagnet 40 may include one or more electrical conductors that are wound around a portion of the anchor socket 36. When the electrical conductors carry electrical current, the electromagnet 40 generates a magnetic field which may strongly attract the first end link 30 and stop the motion thereof. The locking element 38 may further include electronic circuitry such as amplifiers and conversion circuits that convert voltage to current.

The first anchor 26 may be attached to the head component 24. For embodiments in which there is only one linkage element 16, the first anchor 26 may be attached at a base of the head component 24 on a rear side, roughly in the center. For embodiments in which there are three linkage elements 16, the device 10 may include a left first anchor 26A, a right first anchor 26B, and a center first anchor 26C. The left first anchor 26A may be attached to the left side of the head component 24, generally in the vicinity of the left ear. The right first anchor 26B may be attached to the right side of the head component 24, generally in the vicinity of the right ear. The center first anchor 26C may be attached to the base of the head component 24 on the rear side, roughly in the center. The attachment of the first anchor 26 to the head component 24 is usually rigid and may be accomplished with a plurality of connectors, such as snaps, a plurality of fasteners, such as screws, or the like. In some embodiments, the first anchor 26 may be integrally formed as part of the head component 24.

The second anchor 28, as seen in FIGS. 1-3 and 5, generally retains the second end link 32. The second anchor 28 may have substantially the same structure as the first anchor 26 and may include an anchor socket 42, a locking element 44, and an electromagnet 46 that function in a substantially similar fashion to the same-named components of the first anchor 26.

The second anchor 28 may be attached to the body component 22. For embodiments in which there is only one linkage element 16, the second anchor 28 may be attached along or near the center of the body component 22. Alternatively, the second anchor 28 may connect to body equipment such as body armor, a flak jacket, or the like, when the body component 22 is not needed. For embodiments in which there are three linkage elements 16, the device 10 may include a left second anchor 28A, a right second anchor 28B, and a center second anchor 28C. The left second anchor 28A may be coupled to body equipment, generally at the left shoulder. The right second anchor 28B may be coupled to body equipment, generally at the right shoulder. The center second anchor 28C may be attached to the body component 22, typically along or near the center of the body component 22. Alternatively, the center second anchor 28C may connect to body equipment, when the body component 22 is not needed.

As with the first anchor 26, the attachment of the second anchor 28 to the body component 22 is usually rigid and may be accomplished with a plurality of connectors, such as snaps, a plurality of fasteners, such as screws, or the like. In certain embodiments, the second anchor 28 may be integrally formed as part of the body component 22. In other embodiments, the first anchor 26 and the second anchor 28 may be of the same dimension so that part of the linkage element 16 may be readily replaced or repaired with components from another part of the linkage element 16. This configuration may provide an advantage for soldiers in combat situations.

The first end link 30, as seen in FIGS. 1-3 and 5, may include a first ball component 48, a second ball component 50, and a shaft 52. The first ball component 48 and the second ball component 50 may each be roughly spherical shaped and may each include a circular opening on an outer surface. In addition, the first ball component 48 and the second ball component 50 may be formed from a magnetic metal, such as iron or steel. The shaft 52 may be roughly cylindrical shaped and may be hollow or solid. A first end of the shaft 52 may be positioned in the opening of the first ball component 48 and rigidly coupled thereto. An opposing second end of the shaft 52 may be positioned in the opening of the second ball component 50 and rigidly coupled thereto.

The first end link 30 may be positioned such that the first ball component 48 is retained in the anchor socket 36 of the first anchor 26. In some embodiments, the first ball component 48 and the second ball component 50 may be interchangeable, such that the second ball component 50 is retained in the anchor socket 36. As mentioned above, the first end link 30 may be able to rotate, pivot, or move in a conical fashion with respect to the first anchor 26 until the locking element 38 locks the first end link 30 in position.

The second end link 32, as seen in FIGS. 1-3 and 5, may be substantially similar to the first end link 30 and may include a first ball component 54, a second ball component 56, and a shaft 58 that are substantially similar to the same-named components of the first end link 30. The second end link 32 may be positioned such that the first ball component 54 is retained in the anchor socket 42 of the second anchor 28. In some embodiments, the first ball component 54 and the second ball component 56 may be interchangeable, such that the second ball component 56 is retained in the anchor socket 42. Furthermore, the second end link 32 may be able to rotate, pivot, or move in a conical fashion with respect to the second anchor 28 until the locking element 44 locks the second end link 32 in position.

The middle link 34, as seen in FIGS. 1-3 and 5, may include a first socket 60, a second socket 62, and a shaft 64. The first socket 60 may include a concave, partially spherical chamber which is configured to retain at least a portion of the first end link 30, specifically, either the first ball component 48 or the second ball component 50. The first end link 30 and the middle link 34 may be able to rotate, pivot, or move in a conical fashion with respect to one another. The second socket 62 may be substantially similar to the first socket 60 in structure and may be configured to retain at least a portion of the second end link 32, specifically, either the first ball component 54 or the second ball component 56. The second end link 32 and the middle link 34 may be able to rotate, pivot, or move in a conical fashion with respect to one another. In various embodiments, the first socket 60 and the second socket 62 may be interchangeable such that the first socket 60 retains a portion of the second end link 32 and the second socket 62 retains a portion of the first end link 30. The shaft 64 may be roughly cylindrical shaped and may be hollow or solid. A first end of the shaft 64 may rigidly couple to the first socket 60, while an opposing second end of the shaft 64 may rigidly couple to the second socket 62.

In various embodiments, the end links 30, 32 may be removable from the anchors 26, 28 such that the user can easily disengage the body component 22 from the head component 24. Thus, first ball component 48 may be removable from first anchor socket 36, and first ball component 54 may be removable from second anchor socket 42.

The processing element 18, as seen in FIG. 6, may include processors, microprocessors, microcontrollers, digital signal processors (DSPs), field-programmable gate arrays (FPGAs), analog and/or digital application-specific integrated circuits (ASICs), or the like, or combinations thereof. The processing element 18 may generally execute, process, or run instructions, code, code segments, software, firmware, programs, applications, apps, processes, services, daemons, or the like, or may step through states of a finite-state machine. The processing element 18 may be operably coupled to the memory element 20. In some embodiments, the processing element 18 may further include or be in communication with a wireless receiver configured to receive sensor measurements from the wireless transmitter coupled to the second sensor 14.

The processing element 18 may receive sensor measurements from the first sensor 12 and the second sensor 14 and may determine, among other things, if the sensors 12, 14 indicate the presence of a potentially dangerous and injurious impact force. The processing element 18 may receive at least three linear acceleration measurements, at least three angular acceleration measurements, or a combination of both. In some embodiments, the processing element 18 may calculate a magnitude and direction of the acceleration or motion of the head based on the sensor measurements. The magnitude and direction calculation may include a linear acceleration as well as an angular or rotational acceleration. The processing element 18 may consider the magnitude and direction separately and may determine whether the magnitude is greater than or equal to an injury level—i.e., a level at which damage to the recipient may occur. If so, then the processing element 18 may generate or assert a locking signal that is transmitted to the one or more linking elements 16. If the magnitude is less than the injury level, then the processing element 18 may do nothing. For example, the processing element 18 may generate the locking signal if the value of the linear acceleration is greater than or equal to, say, 50 G (the acceleration due to the Earth's gravity) in any direction. In some cases, the injury level value of the magnitude may change depending on the direction, so that the injury level may be 50 G in some directions and greater than 50 G in other directions. To continue the example, the processing element 18 may generate the locking signal if the value of the angular acceleration is greater than or equal to, say, 4000 rad/sec$^2$ in any direction. As with the linear acceleration, the injury level magnitude may change depending on the direction.

In other embodiments, the processing element 18 may evaluate the sensor measurements individually. If the measurements include linear acceleration values such as along the X, Y, and Z axes, then the processing element 18 may generate the locking signal if the linear acceleration value along any of the axes is above the injury level. Alternatively, each axis may have its own injury level value, so that there is an X-axis injury level, a Y-axis injury level, and a Z-axis injury level. Accordingly, the processing element 18 may generate the locking signal if the linear acceleration value along the X-axis is greater than or equal to the X-axis injury level or if the linear acceleration value along the Y-axis is greater than or equal to the Y-axis injury level or if the linear acceleration value along the Z-axis is greater than or equal to the Z-axis injury level or combinations thereof. Furthermore, the processing element 18 may apply an algorithm or a set of steps to the linear acceleration values to determine whether to generate the locking signal.

If the measurements include angular acceleration values such as about the pitch, roll, and yaw axes, then the processing element 18 may generate the locking signal if the angular acceleration value about any of the axes is above the injury level. In some cases, the value of the angular acceleration about the roll axis may be considered most critical. Thus, the processing element 18 may generate the locking signal if the angular acceleration value is greater than or equal to the injury level even if the other values are less than the injury level. As with the linear acceleration values, each axis may have its own injury level value, so that there is a pitch-axis injury level, a roll-axis injury level, and a yaw-axis injury level. Accordingly, the processing element 18 may generate the locking signal if the linear acceleration value about the pitch-axis is greater than or equal to the pitch-axis injury level or if the linear acceleration value about the roll-axis is greater than or equal to the roll-axis injury level or if the linear acceleration value about the yaw-axis is greater than or equal to the yaw-axis injury level or combinations thereof. Furthermore, the processing element 18 may apply an algorithm or a set of steps to the angular acceleration values to determine whether to generate the locking signal.

The locking signal generated by the processing element 18 may include a binary data value, a binary logic level, a pulse-width modulated signal, a voltage value, a current value, or the like. Furthermore, the processing element 18 may include or have access to timer or clock circuitry, which may be utilized in order for the processing element 18 to generate the locking signal for a predetermined time period. In various embodiments, the period for the locking signal may range from approximately 100 milliseconds (ms) to approximately 300 ms (although the most critical period for the locking action is close to 100 milliseconds).

The memory element 20, as seen in FIG. 6, may include data storage components such as read-only memory (ROM), programmable ROM, erasable programmable ROM, random-access memory (RAM), hard disks, floppy disks, optical disks, flash memory, thumb drives, universal serial bus (USB) drives, or the like, or combinations thereof. The memory element 20 may include, or may constitute, a "computer-readable medium". The memory element 20 may store the instructions, code, code segments, software, firmware, programs, applications, apps, services, daemons, or the like that are executed by the processing element 18. The memory element 20 may also store settings, data, documents, sound files, photographs, movies, images, databases, and the like. The processing element 18 may be in communication with the memory element 20 through address busses, data busses, control lines, and the like. In various embodiments, the processing element 18 and memory element 20 may be positioned with or packaged with the first sensor 12.

The body component 22, as seen in FIGS. 1-3, generally provides load bearing contact with the body and may be formed from semi-rigid materials such as hardened plastics, although portions of the body component 22 could be flexible. Accordingly, the body component 22 may be not only sufficiently rigid to be effective for energy dissipation but also sufficiently flexible to be comfortable to the user. The body component 22 may include an elongated bar that extends across the width of the user's back at the shoulder level. The body component 22 is generally worn underneath protective equipment such as shoulder pads, commonly utilized in American football, or such as a body armor, commonly utilized in military combat apparel. The body component 22 may further include padding or foam material to provide comfort to the user. The body component 22 may be connected rigidly or removably to the second anchor 28.

The device 10 may operate as follows. The first sensor 12 may be installed within the head component 24, either positioned between the inner surface of the head component 24 and the user's head or connected to padding on the interior of the head component 24. If utilized, the second sensor 14 may be coupled to or integrated with a mouthguard, which is worn in the user's mouth. For embodiments in which there is one linkage element 16, the first anchor 26 may be attached to the head component 24, and the second anchor 28 may be attached to the body component 22. For embodiments with more than one linkage element 16, at least the left first anchor 26A and the right first anchor 26B may be attached to the head component 24 and the left second anchor 28A and the right second anchor 28B may be attached to body equipment.

The first sensor 12 and the second sensor 14 may measure the force of impacts on the head component 24 and may communicate the sensor measurements to the processing element 18 at frequency rates ranging from 500 Hz to 20 kilohertz (kHz) or higher. While the values of the sensor measurements are less than the injury level (which should be most of the time), the linkage element 16 may be fully flexible—allowing the head component 24 nearly complete freedom of movement with respect to the body component 22.

When the head component 24 receives an impact with a force that could potentially cause traumatic brain injury to the user, then various components of the sensor measurements from the first sensor 12 and/or the second sensor 14 have a value greater than or equal to the injury level. In some embodiments, there may be more than one injury level value associated with the sensor measurements. The processing element 18 receives the sensor measurements and makes a determination as to whether the injury levels have been reached or exceeded using the methods and techniques described above. Upon determination that a dangerous impact has occurred, the processing element 18 may generate or assert the locking signal to the locking elements 38, 44 of the first anchor 26 and the second anchor 28 of the one or more linkage elements 16. The locking signal may activate or energize the electromagnets 40, 46, which generate a strong force of attraction to the first ball components 48, 54 of the first end link 30 and the second end link 32. As a result, the first end link 30 and the second end link 32 may be locked in their position just after the impact was received. Furthermore, with the first end link 30 and the second end link 32 locked in position, the middle link 34 may become locked in position as well, rendering the entire chain of the one or more linkage elements 16 rigid. When the one or more linkage elements 16 are rigid, the head component 24 becomes rigidly integrated with the body component 22 such that energy imparted to the head component 24 is transferred to the body component 22 and absorbed by the body. This also reduces the magnitude of the acceleration or deceleration of the head, thereby reducing the possibility or severity of concussive traumatic brain injury. For embodiments with more than one linkage element 16, the left linkage element 16A and the right linkage element 16B being positioned on the left and right sides of the head may provide a greater reduction of the magnitude of the acceleration or deceleration of the head from side impacts.

Mechanisms other than electromagnets may also be utilized in order to generate the necessary rigidity for energy dissipation. These mechanisms may include, but are not limited to, linear solenoids with fast respond times, among others.

The duration of the transmission or assertion of the locking signal, and thus the rigidity of the one or more linkage elements 16, may range from approximately 100 ms to approximately 400 ms. After that time period, the locking signal is no longer transmitted or asserted, and the one or more linkage elements 16 are again flexible.

Figure 7:
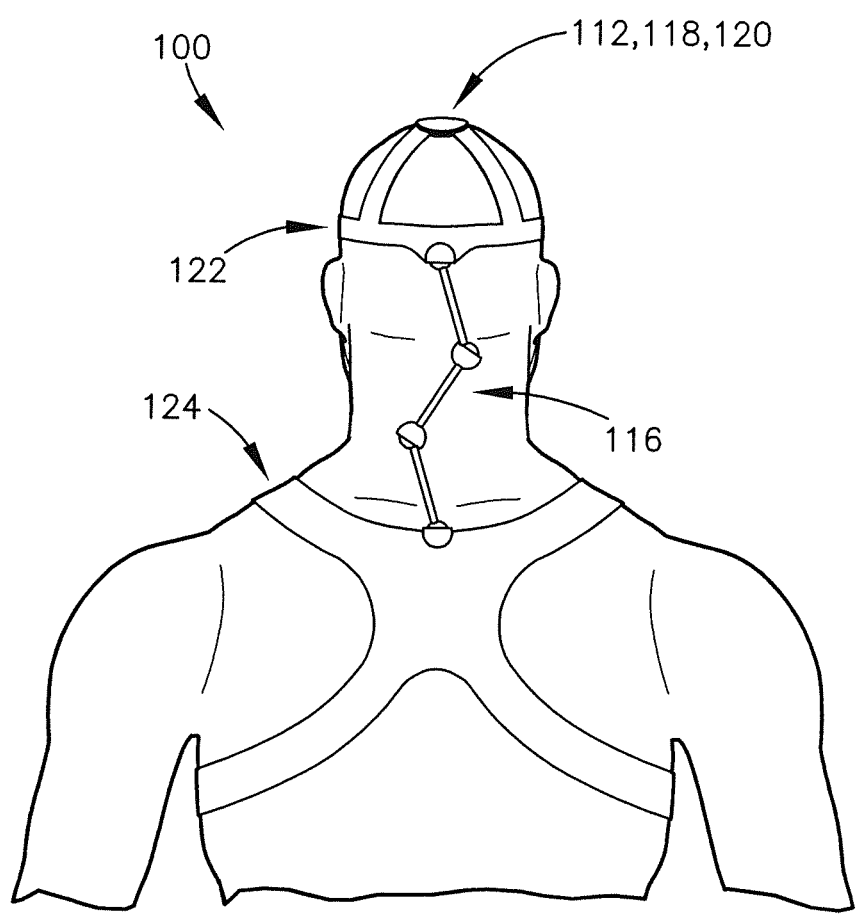
FIG. 7 is a rear view of a system for reducing traumatic brain injury constructed in accordance with a second embodiment of the current invention.
Figure 5:
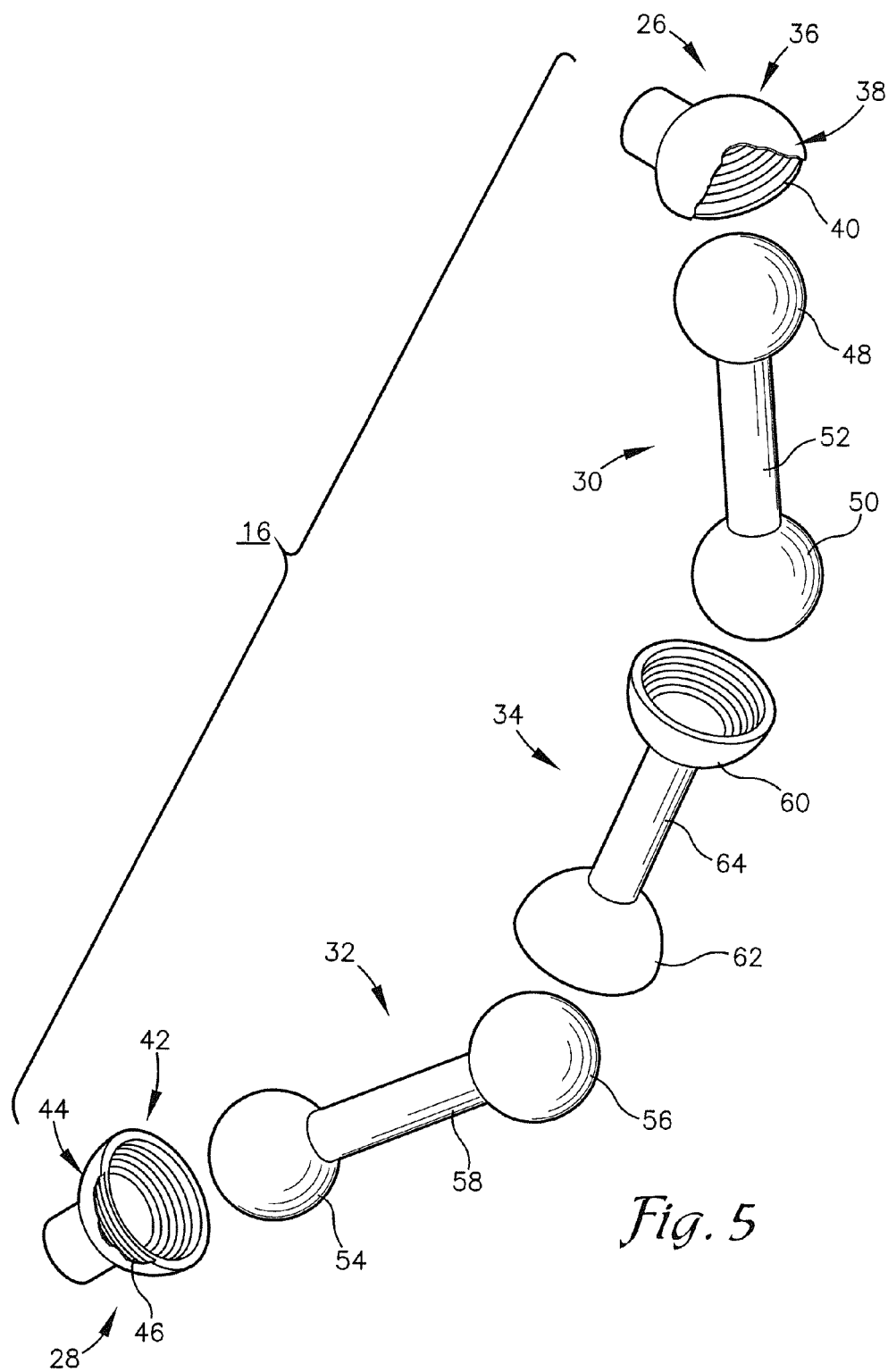
FIG. 5 is a perspective, exploded view of the linkage mechanism of the device of FIG. 1.

A system 100 for reducing traumatic brain injury constructed in accordance with a second embodiment of the current invention is shown in FIG. 7 and broadly comprises a first sensor 112, a second sensor 114, one or more linkage elements 116, a processing element 118, a memory element 120, a head component 122, and a body component 124. The system 100 may be utilized by a user engaging in activity that does not normally include a head component or a body component, such as some forms of boxing, wrestling, and martial arts.

The first sensor 112, the second sensor 114, the one or more linkage elements 116, the processing element 118, and the memory element 120 are substantially similar to the first sensor 12, the second sensor 14, the one or more linkage elements 16, the processing element 18, and the memory element 20 of the device 10.

The head component 122 is generally worn on the head of the user. Typically, the head component 122 covers at least a portion of the top, the sides, and the rear of the head. In some embodiments, the head component 122 may include a plurality of rigid or semi-rigid straps that cover the crown and a portion of the top of the head. In other embodiments, the head component 122 may include headgear, a helmet, or the like. The head component 122 may also retain the first sensor 112 and the processing element 118.

The body component 124 is generally worn on the body of the user. In some embodiments, the body component 124 may include a body harness with a plurality of rigid or semi-rigid straps extending from the back of the upper torso to the front of the upper torso of the user over the shoulders and/or under the arms. In other embodiments, the body component 124 may include shoulder pads, a ballistic vest, body armor, or the like. In all embodiments, the body component 124 may be not only sufficiently rigid to be effective for energy dissipation but also sufficiently flexible to be comfortable to the user.

The one or more linkage elements 116 may couple to the head component 122 and the body component 124 in a similar fashion to the one or more linkage elements 16 and the head component 24 and the body component 22 in the device 10 described above.

The system 100 may operate as follows. The head component 122 and the body component 124 may be worn by the user. The second sensor 114, if utilized, may be integrated with a mouthpiece which is worn in the user's mouth. The rest of the system 100 may function in a substantially similar fashion to the device 10, discussed above. In summary, if the processing element 118 determines an impact to the head that is at or above the injury level, then the processing element 118 may send a locking signal to the one or more linkage elements 116 to render them rigid for approximately 100 ms to approximately 400 ms. Afterwards, the locking signal is no longer transmitted or asserted, and the one or more linkage elements 116 are again flexible.

Figure 9:
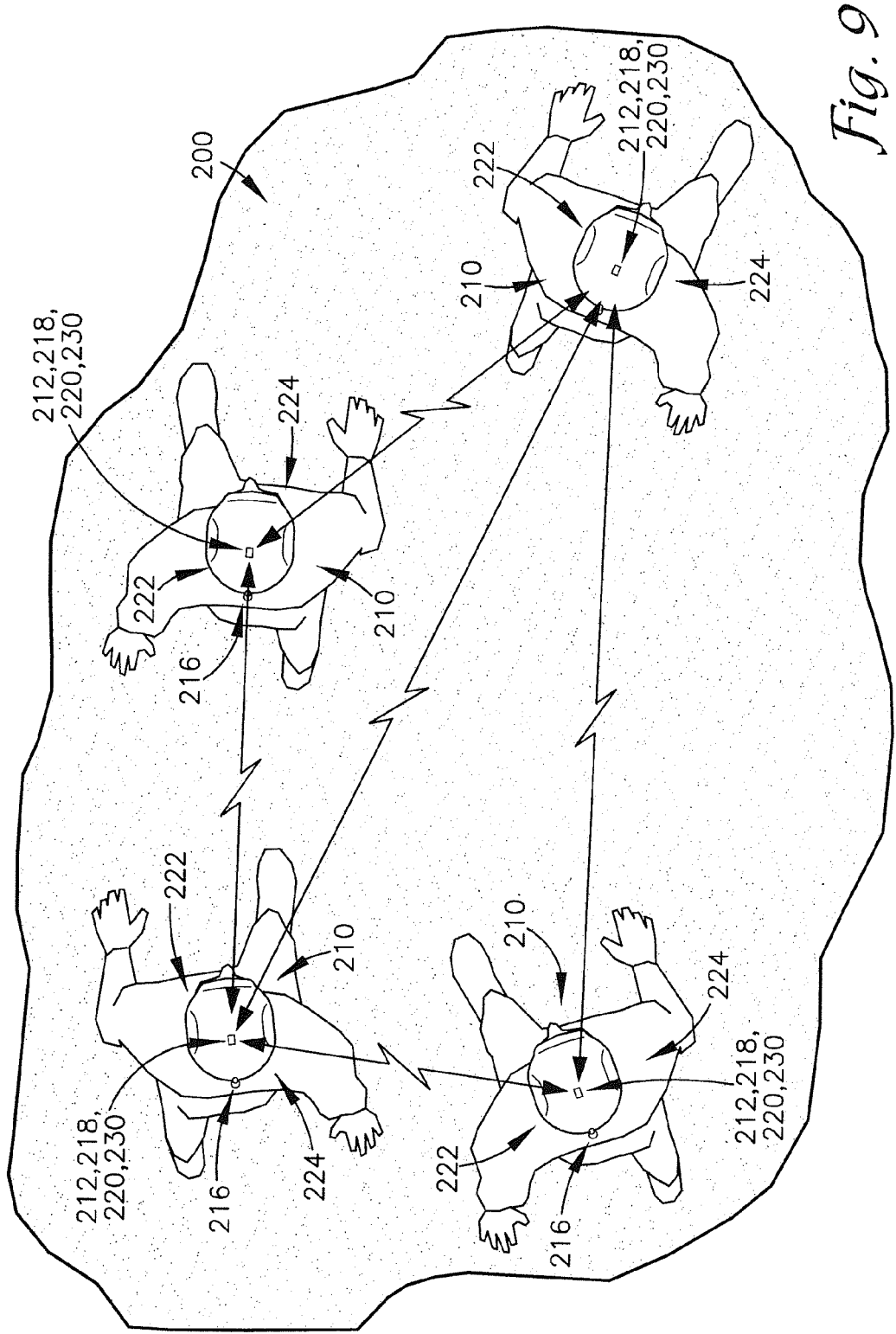
FIG. 9 is an overhead view of a system for reducing traumatic brain injury for a group of people constructed in accordance with a third embodiment of the current invention.

A system 200 for reducing traumatic brain injury for a group of people constructed in accordance with a third embodiment of the current invention is shown in FIG. 9 and broadly comprises a plurality of devices 210 and a plurality of wireless transceivers 230. The system 200 may be utilized by a group of military or law enforcement personnel who are actively engaging hostile parties in a situation where an attack may be imminent. The members of the group may be in close proximity to one another such that an impact on one member of the group may be felt by other members of the group. Typically, each member of the group is wearing a head component 222 such as a helmet and a body component 224 such as ballistic vests, flak jackets, body armor, and the like.

Figure 10:
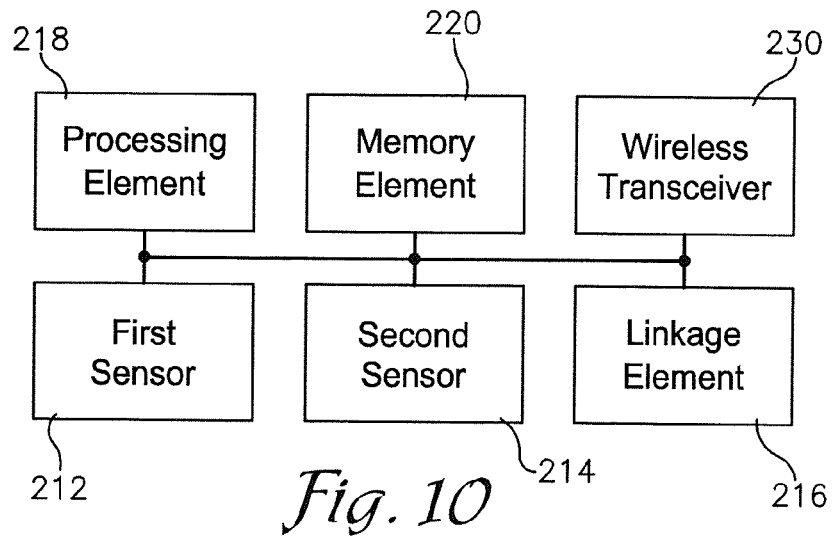
FIG. 10 is a schematic block diagram of other components of the system of FIG. 9.

Each device 210, as seen in part in FIGS. 9 and 10, may be substantially similar to the device 10 and may include a first sensor 212, a second sensor 214, one or more linkage elements 216, a processing element 218, and a memory element 220, which are all substantially similar to the like-named components described above. Each member of the group may be wearing the device 210. Furthermore, the device 210 may couple to the head component 222 and the body component 224 in a similar fashion to the device 10 with the head component 22 and the body component 24 described above.

Each wireless transceiver 230, as seen in FIGS. 9 and 10, may include antennas, signal or data receiving circuits, and signal or data transmitting circuits. The wireless transceiver 230 may transmit and receive radio frequency (RF) signals and/or data and may operate utilizing communication standards such as cellular 2G, 3G, or 4G, Institute of Electrical and Electronics Engineers (IEEE) 802.11 standard such as Wi-Fi, IEEE 802.16 standard such as WiMAX, Bluetooth™, or combinations thereof. Each wireless transceiver 230 may be integrated with or packaged with the processing element 218 and/or the first sensor 212 of each device 210.

Each wireless transceiver 230 may be in communication with the processing element 218 for one device 210. The processing element 218 may communicate a locking signal to the wireless transceiver 230, which may wirelessly transmit the locking signal to the other wireless transceivers 230 in the area. In some embodiments, the wireless transceiver 230 may not transmit the locking signal itself, but rather a signal or data that corresponds to the locking signal. The wireless transceivers 230 of other group members may receive the locking signal and communicate it to the associated processing element 218, the associated one or more linkage elements 216, or both. Furthermore, in certain embodiments, each wireless transceiver 230 may act as a repeater, wherein if a wireless transceiver 230 receives the locking signal, then it may transmit the locking signal as well. Thus, the transmission range of the system 200 is increased by having all of the wireless transceivers 230 transmit the locking signal whenever any device 210 detects a threatening impact.

The system 200 may operate as follows. Each device 210 may be installed or implemented and worn in a similar fashion to the device 10 described above. Given that each wireless transceiver 230 is coupled to a device 210, the wireless transceiver 230 is worn as well. The first sensor 212 and the second sensor 214 of each device may function similarly to the like-named components of the device 10, measuring the acceleration resulting from impacts to the head of each group member.

When the first sensor 212 or the second sensor 214 of one group member measures a significant impact and the processing element 218 determines that the sensor measurement is at or above the injury level, then the processing element 218 may generate or assert the locking signal and communicate it to the associated one or more linkage elements 216. In turn, the one or more linkage elements 216 of the directly impacted group member may become rigid, as described above for the device 10. The processing element 218 may also communicate the locking signal to the associated wireless transceiver 230, which in turn may broadcast the locking signal to the other wireless transceivers 230 in the vicinity.

Each wireless transceiver 230 within range of the originating wireless transceiver 230 may receive the locking signal. In some embodiments, each wireless transceiver 230, upon receipt of the locking signal, may transmit the locking signal as well, thereby increasing the effective range of the system 200. On each device 210, the wireless transceiver 230 may communicate the locking signal to the associated one or more linkage elements 216, which in turn may become rigid just as if the locking signal were received from the associated processing element 218. Thus, the linkage elements 216 for all devices 210 in the vicinity of the originating device 210 may become rigid as a result of the impact experienced by the originating device 210. In effect, an impact on one member of the group becomes an impact to all members of the group. In various embodiments, the linkage elements 216 may remain rigid for a longer period of time as compared with the linkage elements 16 of the device 10. For example, the linkage elements 216 may remain rigid for 3-5 seconds before becoming flexible again.

Figure 11:
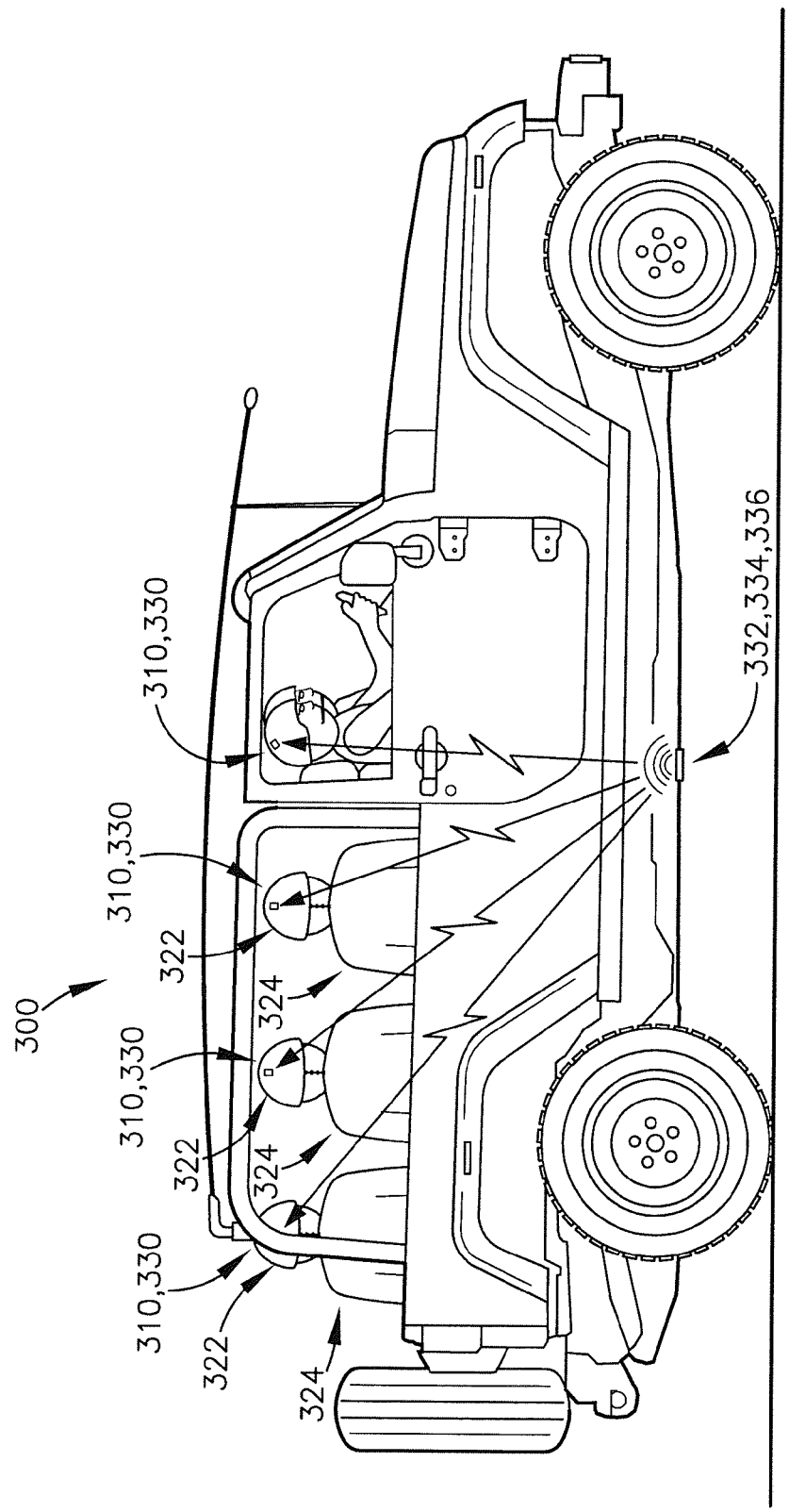
FIG. 11 is a side view of a system for reducing traumatic brain injury for a group of people in a vehicle constructed in accordance with a fourth embodiment of the current invention.

A system 300 for reducing traumatic brain injury for a group of people in a vehicle constructed in accordance with a fourth embodiment of the current invention is shown in FIG. 11 and broadly comprises a plurality of devices 310, a plurality of wireless transceivers 330, a vehicle sensor 332, a vehicle processing element 334, and a vehicle transmitter 336. In various embodiments, each wireless transceiver 330 may be included or integrated as a component of a device 310. The system 300 may be utilized by a group of military or law enforcement personnel who are in a vehicle which is located in or traveling in a hostile area where the vehicle could come under attack either from airborne projectiles, such as bullets or grenades, or roadway hazards, such as improvised explosive devices or mines. Each member of the group may be wearing a device 310, a head component 322, a body component 324, and a wireless transceiver 330.

The devices 310, including linkage elements 316, and the wireless transceivers 330 may be substantially similar to the devices 210, the linkage elements 216, and the wireless transceivers 230 of the system 200. Furthermore, the devices 310 may couple to and interact with the head components 322 and the body components 324 in a similar fashion as the like-named components discussed above for the system 200.

Figure 12:
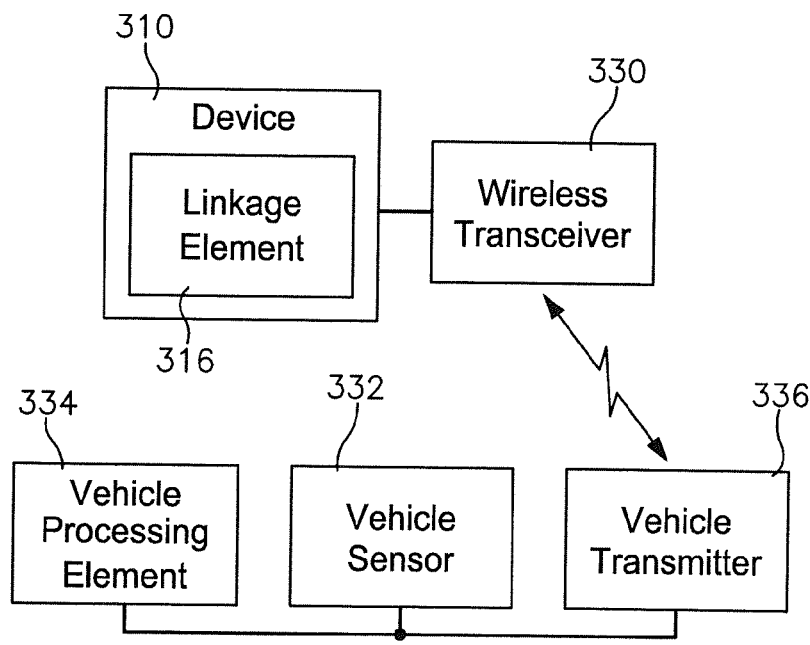
FIG. 12 is a schematic block diagram of other components of the system of FIG. 11.

The vehicle sensor 332, as seen in FIGS. 11 and 12, may be substantially similar in structure and function to the first sensor 12 or the second sensor 14 of the device 10 and may measure an acceleration of the vehicle or portions of the vehicle due to an impact. The vehicle sensor 332 may additionally or alternatively measure a velocity of or a force on the vehicle. The vehicle sensor 332 may generate vehicle sensor measurements of the acceleration, velocity, or force. The vehicle sensor 332 may be coupled to the body of the vehicle such as panels or walls on the sides, the front, the rear, the roof, or the undercarriage. In certain embodiments, the system 300 may comprise a plurality of vehicle sensors 332 positioned in various locations on the body of the vehicle.

The vehicle processing element 334, as seen in FIGS. 11 and 12, may be substantially similar in structure and function to the processing element 18 of the device 10 and may receive vehicle sensor measurements from the vehicle sensor 332. The vehicle processing element 334 may determine whether the value of the vehicle sensor measurement is above a critical level at which the vehicle may be damaged and the group members within may be injured. When the value of the vehicle sensor measurement (or any of the vehicle sensor measurements, if more than one vehicle sensor 332 is present) is above the critical level, the processing element 334 may generate or assert a locking signal, which is substantially similar to the locking signal of the device 10.

The vehicle transmitter 336, as seen in FIGS. 11 and 12, generally transmits signals and/or data wirelessly utilizing known RF communication standards. The vehicle transmitter 336 may be in communication with the vehicle processing element 334 and may receive the locking signal therefrom. In other embodiments, the vehicle transmitter 336 may be in communication with the vehicle sensor 332 and may receive the sensor measurements therefrom. The vehicle transmitter 336 may wirelessly transmit the locking signal or the vehicle sensor measurements to the wireless transceivers 330 worn by each member of the group.

The vehicle transmitter 336 may be integrated with or packaged with the vehicle processing element 334 and/or the vehicle sensor 332. In embodiments of the system 300 with a plurality of vehicle sensors 332, there may be a plurality of vehicle transmitters 336, one vehicle transmitter 336 for each vehicle sensor 332, or there may be one vehicle transmitter 336, such that all of the vehicle sensors 332 are connected to the vehicle transmitter 336 through electrical wires or cables.

The system 300 may operate as follows. The devices 310 and the wireless transceivers 330 may be implemented and may operate in a substantially similar fashion to the like-named components of the system 200. The vehicle sensor 332 may be making measurements of the acceleration, velocity, or force affecting the vehicle on a regular basis and communicating the vehicle sensor measurements to the vehicle processing element 334. When the vehicle processing element 334 determines that a value of the vehicle sensor measurement is at or above the critical level, the vehicle processing element 334 may generate or assert the locking signal to the vehicle transmitter 336, which in turn broadcasts the locking signal to the wireless transceivers 330 of all of the members of the group. Each wireless transceiver 330 may communicate the locking signal to its associated one or more linkage elements 316, rendering the linkage elements 316 rigid. Thus, when the vehicle comes under attack, the head component 322 and body component 324 of each member of the group may become rigidly integrated in order to protect the members from possible traumatic brain injury as a result of vehicular damage or overturning of the vehicle. As with the system 200, the linkage elements 316 may remain rigid for 3-5 seconds before becoming flexible again.

Figure 13:
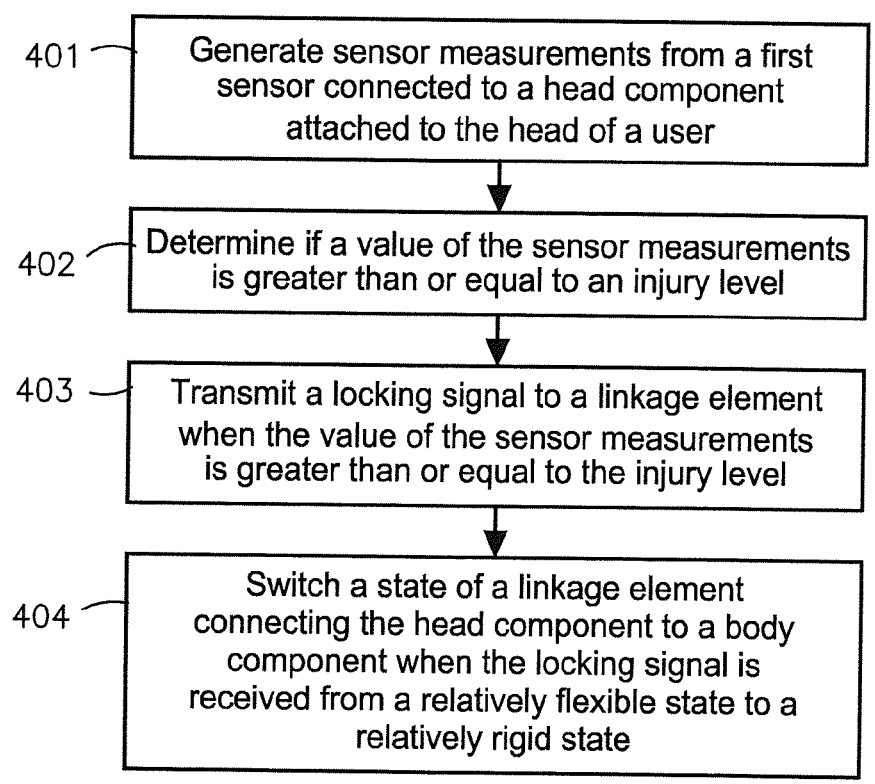
FIG. 13 is a flow diagram of at least a portion of the steps of a method of reducing traumatic brain injury in accordance with a fifth embodiment of the current invention.

At least a portion of the steps of a method 400, in accordance with a fifth embodiment of the current invention, of reducing traumatic brain injury is shown in FIG. 13. The steps may be performed in the order presented in FIG. 13, or they may be performed in a different order. In addition, some of the steps may be performed simultaneously instead of sequentially. Furthermore, some steps may not be performed.

Referring to step 401, sensor measurements are generated from a first sensor 12. The sensor measurements may include a linear acceleration or an angular acceleration. The first sensor 12 may include accelerometers or other devices that measure velocities, accelerations, or forces. The first sensor 12 may be coupled or attached to a head component 24, which may include a helmet worn on a user's head. Thus, the first sensor 12 may measure a linear or angular acceleration of a user's head as the result of an impact or blow to the head. The sensor measurements may be received by a processing element 18.

Referring to step 402, it is determined if a value of the sensor measurements is greater than or equal to one or more injury levels. The sensor measurements may include three orthogonal-axis linear or angular values from which the processing element 18 may determine whether the injury levels have been reached or exceeded using the methods and techniques described above for the device 10. An example of injury level values may include 50 G or 4000 rad/sec$^2$.

Referring to step 403, a locking signal is transmitted to a linkage element 16 when the value of the sensor measurements is greater than or equal to the injury level. The locking signal may include a binary data value, a binary logic level, a pulse-width modulated signal, a voltage value, a current value, or the like.

Referring to step 404, a state of the linkage element 16 is switched from a relatively flexible state to a relatively rigid state. The linkage element 16 may be formed from material or components whose stiffness or rigidity can be controlled, that is, increased and decreased. In exemplary embodiments, the linkage element 16 may be formed from a plurality of components and may include a first anchor 26, a second anchor 28, a first end link 30, a second end link 32, and at least one middle link 34, as shown in FIGS. 1-3 and 5 and discussed above. One end of the linkage element 16 may be connected to the head component 24 while the opposite end may be connected to a body component 22. The body component 22 may include shoulder pads, body armor, or the like.

Under normal circumstances, the linkage element 16 is flexible and the links 30, 32, 34 may rotate freely with respect to one another and with respect to the anchors 26, 28 such that the linkage element 16 may assume a variety of shapes and positions. The head component 24 and the body component 22 may also move with respect to one another. When the linkage element 16 receives the locking signal from the processing element 18, the linkage element 16 becomes rigid and retains its current shape and position. Typically, the linkage element 16 remains rigid for approximately 100 ms to approximately 400 ms. The first and second anchors 26, 28 each include a locking element 38, 44 that locks the links 30, 32, 34 in their current positions. Furthermore, with the linkage element 16 momentarily locked in position, the head component 24 and the body component 22 momentarily maintain their relative positions as well, thereby allowing energy received by the head component 24 to be transferred through the linkage element 16 to the body component 22 to be dissipated.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A method of reducing traumatic brain injury comprising the steps of:
   generating sensor measurements from a first sensor coupled to a head component attached to the head of a user in response to an impact to the user which causes motion of the head;
   determining if a value of the sensor measurements is greater than or equal to an injury level value;
   transmitting a locking signal to a linkage element when the value of the sensor measurements is greater than or equal to the injury level value;
   switching a state of the linkage element connecting the head component to a body component attached to the body of the user when the locking signal is received from a relatively flexible state to a relatively rigid state to stop motion of the head about the neck toward either shoulder of the user; and
   wherein links of the linkage element are operable to rotate with respect to one another and switching the state of the linkage element from the relatively flexible state to the relatively rigid state stops rotational motion of the linkage element.

2. The method of claim 1, wherein each sensor measurement includes a plurality of measured values, each measured value corresponding to an orthogonal axis, and the locking signal is transmitted when one of the measured values is greater than or equal to the injury level value.

3. The method of claim 1, wherein each sensor measurement includes a plurality of measured values, each measured value including an acceleration of the head about the neck toward either shoulder of the user, and the locking signal is transmitted when the measured value is greater than or equal to the injury level value.

4. The method of claim 1, wherein switching the state of the linkage element includes generating a magnetic field from a first component of the linkage element to a second component of the linkage element to lock the relative positions of the first component and the second component.

5. The method of claim 1, wherein the linkage element includes
   a first anchor configured to rigidly couple to the head component,
   a second anchor configured to rigidly couple to the body component,
   a first end link coupled to the first anchor and configured to rotate and pivot with respect to the first anchor,
   a second end link coupled to the second anchor and configured to rotate and pivot with respect to the second anchor, and
   a middle link coupled to the first anchor and the second anchor and configured to rotate and pivot with respect to both the first anchor and the second anchor.

6. The method of claim 5, wherein the first end link locks its position with respect to the first anchor and the second end link locks its position with respect to the second anchor when the locking signal is received.

7. The method of claim 5, wherein switching the state of the linkage element includes generating a magnetic field from the first anchor to the first end link to lock the relative positions of the first anchor and the first end link.

8. The method of claim 5, wherein switching the state of the linkage element includes generating a magnetic field from the second anchor to the second end link to lock the relative positions of the second anchor and the second end link.

9. A method of reducing traumatic brain injury comprising the steps of:
   generating sensor measurements from a first sensor coupled to a head component attached to the head of a user in response to an impact to the user which causes motion of the head;
   determining if a value of the sensor measurements is greater than or equal to an injury level value to indicate the presence of a potentially dangerous and harmful impact force to the head;
   transmitting a locking signal to a linkage element when the value of the sensor measurements is greater than or equal to the injury level value to indicate the presence of a potentially dangerous and harmful impact force to the head, the linkage element including
      a first anchor configured to rigidly couple to the head component,
      a second anchor configured to rigidly couple to the body component,
      a plurality of links coupling the first anchor to the second anchor the links including
         a first end link coupled to the first anchor and configured to rotate and pivot with respect to the anchor,
         a second end link coupled to the second anchor and configured to rotate and pivot with respect to the second anchor, and
         a middle link coupled to the first anchor and the second anchor and configured to rotate and pivot with respect to both the first anchor and the second anchor; and
   switching a state of the linkage element connecting the head component to a body component attached to the body of the user when the locking signal is received from a relatively flexible state to a relatively rigid state, such that motion is stopped between the first anchor and at least one link and between the second anchor and at least one link.

10. The method of claim 9, wherein switching the state of the linkage element includes generating a magnetic field from a first component of the linkage element to a second component of the linkage element to lock the relative positions of the first component and the second component.

11. The method of claim 9, wherein the first end link locks its position with respect to the first anchor and the second end link locks its position with respect to the second anchor when the locking signal is received.

12. The method of claim 9, wherein switching the state of the linkage element includes generating a magnetic field from the first anchor to the first end link to lock the relative positions of the first anchor and the first end link.

13. The method of claim 9, wherein switching the state of the linkage element includes generating a magnetic field from the second anchor to the second end link to lock the relative positions of the second anchor and the second end link.

14. A method of reducing traumatic brain injury comprising the steps of:
generating sensor measurements from a first sensor coupled to a head component attached to the head of a user in response to an impact to the user which causes motion of the head;
determining if a value of the sensor measurements is greater than or equal to an injury level value to indicate the presence of a potentially dangerous and harmful impact force to the head;
transmitting a locking signal to a linkage element connecting the head component to a body component attached to the body of the user when the value of the sensor measurements is greater than or equal to the injury level value to indicate the presence of a potentially dangerous and harmful impact force to the head;
generating a magnetic field from a first component of the linkage element to a second component of the linkage element to lock the relative positions of the first component and the second component when the locking signal is received; and
wherein the magnetic field is generated from the first component of the linkage element to strongly attract the second component of the linkage element.

15. The method of claim 14, wherein the first component of the linkage element is rigidly attached to the head component and the second component of the linkage element is rotatably coupled to the first component when the locking signal is absent.

16. The method of claim 14, further comprising the step of generating a magnetic field from a third component of the linkage element to a fourth component of the linkage element to lock the relative positions of the third component and the fourth component when the locking signal is received.

17. The method of claim 16, wherein the third component of the linkage element is rigidly attached to the body component and the fourth component of the linkage element is rotatably coupled to the third component when the locking signal is absent.

18. The method of claim 14, wherein each sensor measurement includes a plurality of measured values, each measured value corresponding to an orthogonal axis, and the locking signal is transmitted when one of the measured values is greater than or equal to the injury level value.

19. The method of claim 14, wherein each sensor measurement includes a plurality of measured values, each measured value including an acceleration of the head about the neck toward either shoulder of the user, and the locking signal is transmitted when the measured value is greater than or equal to the injury level value.

* * * * *